United States Patent [19]
Young

[11] 3,947,323
[45] Mar. 30, 1976

[54] FERMENTATION PROCESSES

[76] Inventor: Murray Moo Young, 300 Regina St. N., Apt. 1-1206, Waterloo, Ontario, Canada

[22] Filed: Aug. 14, 1974

[21] Appl. No.: 497,306

[52] U.S. Cl................. 195/65; 195/114; 195/36 R; 195/100
[51] Int. Cl.$^2$.......................................... C12D 13/10
[58] Field of Search............. 195/114, 81, 65, 36 R, 195/100

[56] References Cited
UNITED STATES PATENTS

| | | | |
|---|---|---|---|
| 3,293,145 | 12/1966 | Leavitt et al..................... | 195/114 X |
| 3,666,628 | 5/1972 | Dworschack et al. ......... | 195/66 R X |

*Primary Examiner*—Lionel M. Shapiro
*Attorney, Agent, or Firm*—Sim & McBurney

[57] ABSTRACT

Fermentation parameters are improved by the addition of certain polymers to the fermentation broth. Small quantities of carboxypolymethylene in *Aspergillus niger* cultures are particularly effective.

9 Claims, No Drawings

FERMENTATION PROCESSES

FIELD OF INVENTION

This invention relates to the improvement of microbial fermentation processes by the incorporation of certain additives.

BACKGROUND TO THE INVENTION

The addition of various components to microbial fermentation systems to improve the yield of products has previously been proposed. Generally, those prior art procedures have involved the use of various surfactants or nutrients and are concerned with the recovery of specific products.

SUMMARY OF INVENTION

In accordance with the present invention, the fermentation parameters of a culture are enhanced by the addition of small quantities of at least one non-consumable, water-soluble, non-toxic, non-growth inhibiting polymeric nonionic or anionic material consisting wholly of repeating units.

GENERAL DESCRIPTION OF INVENTION

While the present invention is directed more particularly to systems involving filamentous microorganisms the invention also may be used with bacterial and yeast systems and with microorganisms in pellet form. Filamentous microorganisms are those which produce a growth characterized by long, interwoven threads. The actinomycetes and fungi which exemplify these materials include:

i. The *Aspergilli*, which generally are useful in the production of enzymes such as amylase and protease, and of metabolic products, such as citric acid, and include *Aspergillus niger*, ii. The *Penicillia*, which are important as producers of enzymes, such as dextranase, and as producers of antibiotics notably penicillin by such species as *Penicillium notatum* and *Penicillium chrysogenum*, iii. The *Streptomyces*, which are important as producers of enzymes useful in the transformation of steroids, and of antibiotics such as streptomycin novobiocin, and tetracycline, iv. MUcorales including the species of *Rhizopus*, *Cunnighamella* and *Mucor* which are also useful in producing enzyme systems and metabolic products, such as organic acids.

These microorganisms tend to form discrete pellet structures in aerobic submerged fermentations. The present invention causes modification of the biomass structure and enhancement of product formation, as described below.

To the culture in an aqueous nutrient medium of any convenient form, depending on the particular microorganism is added the water soluble polymer in accordance with this invention. Small quantities typically from a trace to 1% of the polymer are used, resulting in enhanced parameters.

The parameters which are of particular interest and which are enhanced by the polymer addition of the present invention are the microbial growth rate and the rate of product formation.

Fermentation processes basically result in the production of one of three types of desired product: the cells themselves, the primary metabolite and the secondary metabolites. The present invention is effective in enhancing the yield of all three types of product, the particular product, of course, depending on the system utilized.

In some instances, therefore, the microbial growth rate and the rate of product formation are the same, while, in many systems, they are different. Improvement in one or both parameters is achieved by the polymer addition of the invention. The presence of the polymer in some way results in modification of the microbial biomass resulting in increased mass transfer of nutrients and/or metabolites between the growing microorganism and the fermentation medium.

The polymers used in the present invention must consist wholly of a repeating unit, resulting in a very low detergency effect and be non-toxic to the microorganism. Further, the polymer must remain unconsumed by the culture, be water-soluble and be non-growth-inhibiting.

Among those materials particularly preferred are high molecular weight carboxypolymethylenes or other carboxyvinyl polymers and polyacrylates, and polyethylene glycol of various molecular weights.

EXAMPLES

The invention is illustrated by the following Examples:

EXAMPLE I

Various polymers were added in a quantity of 3g/l to a culture consisting of *Aspergillus niger*, NRRL 337, in a nutrition medium having a pH of 5 and containing

| | | |
|---|---|---|
| Glucose | 7.0 | g |
| Lactic acid | 3.5 | g |
| (neutralized to pH 7 with NH$_4$OH) | | |
| KH$_2$PO$_4$ | 13.7 | g |
| KNO$_3$ | 2.0 | g |
| MgSO$_4$ | 1.2 | g |
| ZnSO$_4$ 7H$_2$O | 0.002 | g |
| MnSO$_4$ H$_2$O | 0.010 | g |
| FeSO$_4$ 7H$_2$O | 0.010 | g |
| Distilled H$_2$O | 1000 | ml |

The system was inoculated by standard procedure and incubated for a period of about 5 days at 30°C.

The growth rate of the microorganisms as compared to that in a control medium to which no polymer has been added, the amylase production rate as compared to that of the control medium, the change in viscosity of the medium on addition of the polymer, the change in surface tension of the medium upon addition of the polymer and the change in viscosity of the medium from start to finish of the incubation period were measured. During the incubation period, the mycelia in the cultures formed dispersed pulpy growth as compared to the formation of packed hard discrete pellets of 4 to 8 mm diameter in the control medium.

The results are reproduced in the following Table I:

TABLE I

| Polymer | Chemical Type | Relative Growth Rate | Relative Amylase Production Rate | Viscosity change on Polymer addition | Surface tension change on Polymer addition | Viscosity change over incubation period |
|---|---|---|---|---|---|---|
| Carbopol 934 | carboxypolymethylene | 2.65 | 17.5 | 1.1 | 0.9 | 1.2 |
| Carbowax 400 | polyethylene glycol | 2.04 | 12.5 | 1.1 | 0.9 | 1.2 |
| Reten A-1 | polyacrylate | 1.69 | 2.5 | 7.9 | 0.9 | 1.2 |
| Goodrite K-714 | polyacrylate | 2.10 | 4.0 | 1.2 | 1.0 | 1.0 |
| Separon | polyacrylamide | 2.78 | 12.5 | 14.4 | 0.9 | 0.6 |
| Elvanol | polyvinyl alcohol | 1.85 | 1.0 | 1.3 | 0.9 | 1.3 |
| Polyox-205 | polyethylene oxide | 0.37 | 0 | 1.8 | 1.0 | 1.0 |
| Jaguar | polyglycoside | 0.85 | 1.7 | 3.5 | 1.0 | 0.3 |

The results of the above Table I show that only the carboxypolymethylene, the polyethylene glycol and the polyacrylates tested gave the desired results. While the polyacrylamides and the polyglycoside increased growth rate, the viscosity of the solutions had decreased, indicating degradation of the polymers. The polyethylene oxide was toxic to the microorganisms and the polyvinyl alcohol did not improve the amylase production rate. All the tested polymers had a low detergency, as evidenced by the insignificant change in surface tension on addition of the polymer.

EXAMPLE II

Comparative tests were carried out using various surfactants as the additive to the culture medium. The results are reproduced in the following Table II:

TABLE II

| Surfactant | Concentration ppm | Relative Growth Rate | Surface Tension Change |
|---|---|---|---|
| Sodium lauryl sulfate | 200 | 0.52 | 0.7 |
| Span--20 | 200 | 0.85 | 0.5 |
| Tergitol | 50 | 0.59 | 0.6 |
| Antifoam--10 | 20 | 0.40 | 0.7 |
|  | 100 | 0.54 | 0.6 |

The results of the above Table II show generally adverse effects on growth rate and a significant decrease in surface tension with the addition of surfactants. Additionally discrete pellet formation was observed.

EXAMPLE III

The procedure of Example I is repeated utilizing differing quantities of Carbopol 934 as the additive to the culture medium. The results are reproduced in the following Table III:

TABLE III

| Quantity % | Relative Growth Rate | Relative Amylase Production Rate | Viscosity change on Polymer Addition | Viscosity change over Incubation Period |
|---|---|---|---|---|
| 0.1 | 1.09 | 3.3 | 1.0 | 1.2 |
| 0.2 | 1.33 | 3.5 | 1.1 | 1.0 |
| 0.3 | 2.05 | 17.5 | 1.1 | 1.2 |
| 0.4 | 2.07 | 3.6 | 1.1 | 1.1 |
| 0.5 | 2.27 | 6.7 | 1.1 | 1.4 |
| 0.6 | 2.40 | 12.5 | 1.1 | 1.4 |

The results of this Table III show particularly marked improvement in amylase production rate at 0.3 and 0.6% by weight.

EXAMPLE IV

Comparative tests were carried out using cultures with preformed discrete pellets of *Aspergillus niger* to which 0.3% Carbopol was added. The results for two different pellet sizes are reproduced in the following Table IV:

TABLE IV

| Initial Pellet Diameter mm | Relative Growth Rate | Relative Amylase Production Rate |
|---|---|---|
| 6 | 1.47 | 2.82 |
| 8 | 1.23 | 1.82 |

The results of this Table IV indicate that the enhancement effects of the polymer additive are also obtained in cultures with discrete pellet growths.

SUMMARY

The present invention, therefore, provides a procedure for enhancing fermentation parameters by the addition of certain polymers.

I claim:

1. A fermentation process which comprises forming amylase in an aqueous culture containing an Aspergillus species, a nutrient therefor and a small quantity of a polymeric material selected from a carboxypolymethylene, a polyacrylate and a polyethylene glycol.

2. The process of claim 1 wherein the polymeric material is a high molecular weight carboxypolymethylene.

3. The process of claim 1 wherein the polymeric material is a high molecular weight polyacrylate.

4. The process of claim 1 wherein the polymeric material is a polyethylene glycol.

5. The process of claim 1 wherein the polymeric material is added in a quantity from trace to about 1% by weight.

6. The process of claim 1 wherein the polymeric material is a high molecular weight carboxypolymethylene present in a quantity of about 0.3% by weight.

7. The process of claim 1 wherein the microbial growth is in dispersed pulpy form.

8. The process of claim 1 wherein the microbial growth is in discrete pellet form.

9. The process of claim 1 wherein the Aspergillus species is *Aspergillus niger*.

* * * * *